(12) United States Patent
Hoffman

(10) Patent No.: US 10,426,836 B2
(45) Date of Patent: Oct. 1, 2019

(54) COMPOSITIONS AND METHODS FOR TREATING STRESS-RELATED DISORDERS

(71) Applicant: Steven Hoffman, Mahwah, NJ (US)

(72) Inventor: Steven Hoffman, Mahwah, NJ (US)

(73) Assignee: Hoffman Technologies, Inc., Cranford, NJ (US)

( * ) Notice: Subject to any disclaimer, the term of this patent is extended or adjusted under 35 U.S.C. 154(b) by 17 days.

(21) Appl. No.: 15/653,837

(22) Filed: Jul. 19, 2017

(65) Prior Publication Data

US 2019/0022224 A1    Jan. 24, 2019

(51) Int. Cl.
*A61K 45/06* (2006.01)
*A61K 31/198* (2006.01)
*A61K 31/19* (2006.01)
*A61K 31/216* (2006.01)

(52) U.S. Cl.
CPC ............ *A61K 45/06* (2013.01); *A61K 31/19* (2013.01); *A61K 31/198* (2013.01); *A61K 31/216* (2013.01)

(58) Field of Classification Search
None
See application file for complete search history.

(56) References Cited

U.S. PATENT DOCUMENTS

| | | | | |
|---|---|---|---|---|
| 4,165,382 A | * | 8/1979 | Pozuelo | A61K 31/195 514/567 |
| 2001/0047010 A1 | * | 11/2001 | Pozuelo | A61K 31/44 514/310 |
| 2012/0322682 A1 | * | 12/2012 | McDevitt | G01N 33/54313 506/9 |
| 2014/0073562 A1 | * | 3/2014 | Djupesland | A61M 15/08 514/4.8 |
| 2017/0029892 A1 | | 2/2017 | Lombard | |

FOREIGN PATENT DOCUMENTS

| | | |
|---|---|---|
| WO | 2012123819 A1 | 9/2012 |
| WO | 2014045023 A1 | 3/2014 |
| WO | 2014078724 A1 | 5/2014 |

OTHER PUBLICATIONS

Searcy "Pharmacological Prevention of Combat-Related PTSD: A Literature Review," Military Medicine, 177, 6:649, 2012 (Year: 2012).*

Streckler et al. "Pharmacological treatment of PTSD e Established and new approaches," Neuropharmacology 62 (2012) 617-627 (Year: 2012).*

International Search Report and Written Opinion issued in Application No. PCT/US2018/042874, dated Oct. 9, 2018.

Sophie A. George, et al., "Altered locus coeruleus-norepinephrine function following single prolonged stress" European Journal of Neuroscience, vol. 37,No. 6, 2013, XP055510850, pp. 901-909.

Hagit Cohen, et al., "Anisomycin, a Protein Synthesis Inhibitor, Disrupts Traumatic Memory Consolidation and Attenuates Post-traumatic Stress Response in Rats" Biological Psychiatry, vol. 60, No. 7, 2006, XP027916943, pp. 767-776.

* cited by examiner

*Primary Examiner* — Jeffrey S Lundgren
*Assistant Examiner* — Michael J Schmitt
(74) *Attorney, Agent, or Firm* — BakerHostetler

(57) ABSTRACT

The present inventions relate generally to compositions, kits, and methods for the treatment of stress-related disorders, including but not limited to post-traumatic stress disorder.

10 Claims, No Drawings

COMPOSITIONS AND METHODS FOR TREATING STRESS-RELATED DISORDERS

TECHNICAL FIELD

The present inventions relate generally to compositions, kits, and methods for the treatment of stress-related disorders, including but not limited to post-traumatic stress disorder.

BACKGROUND

The American Psychiatric Associate defines post-traumatic stress disorder ("PTSD") as a psychiatric disorder that can occur in people who have experienced or witnessed a traumatic event such as a natural disaster, a serious accident, a terrorist act, war/combat, rape or other violent personal assault. PTSD, once called shell shock or battle fatigue syndrome, typically is a lasting consequence of traumatic ordeals that cause intense fear, helplessness, or horror, such as a sexual or physical assault, the unexpected death of a loved one, an accident, war, or natural disaster. Families of victims can also develop PTSD, as can emergency personnel and rescue workers.

Most people who experience a traumatic event will have reactions that include shock, anger, nervousness, fear, and even guilt. For most people, these feelings they go away over time. But for a person with PTSD, these feelings continue and even increase, becoming so strong that they keep the person from living a normal life.

Those suffering from PTSD typically have abnormal levels of stress hormones. Studies have shown that individuals with PTSD have lower levels of cortisol than those who do not have PTSD and higher than average levels of epinephrine and norepinephrine.

SUMMARY

The present invention provides methods, compositions, and kits for treating PTSD and other stress-related disorders in a subject in need thereof. In certain embodiments, the methods comprise administering to the subject an effective amount of a tyrosine hydroxylase inhibitor. In other embodiments, the invention provides methods that further comprise administering to the subject an effective amount of one or more stress modulators such as vasopressin, vasopressin derivatives, acetylcholine inducers, γ-aminobutyric acid (GABA), and other agents known to be useful in the treatment of anxiety or agitation.

The present invention also provides methods for reducing the level one or more of epinephrine and norepinephrine in a subject in need thereof. In certain embodiments, the methods comprise administering to the subject an effective amount of a tyrosine hydroxylase inhibitor. In other embodiments, the invention provides methods that further comprise administering to the subject an effective amount of a tyrosine hydroxylase inhibitor and one or more stress modulators.

In still further embodiments, the invention provides pharmaceutical compositions comprising a tyrosine hydroxylase inhibitor and one or more stress modulators. Also provided are kits comprising a tyrosine hydroxylase inhibitor and one or more stress modulators together with packaging for same.

DETAILED DESCRIPTION OF ILLUSTRATIVE EMBODIMENTS

The present subject matter may be understood more readily by reference to the following detailed description which forms a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, another embodiment incudes from the one particular and/or to the other particular value. Similarly, when values are expressed as approximations, by use of the antecedent "about," it is understood that the particular value forms another embodiment. All ranges are inclusive and combinable.

As used herein, the terms "component," "composition," "composition of compounds," "compound," "drug," "pharmacologically active agent," "active agent," "therapeutic," "therapy," "treatment," or "medicament" are used interchangeably herein to refer to a compound or compounds or composition of matter which, when administered to a subject (human or animal) induces a desired pharmacological and/or physiologic effect by local and/or systemic action.

As used herein, the terms "treatment" or "therapy" (as well as different forms thereof) include preventative (e.g., prophylactic), curative or palliative treatment. As used herein, the term "treating" includes alleviating or reducing at least one adverse or negative effect or symptom of a condition, disease or disorder. This condition, disease or disorder can be intestinal hyperpermeability.

With respect to PTSD, for example, the adverse or negative effect or symptoms can include any of those that are the subject of the diagnostic criteria specified for PTSD in the American Psychiatric Association's Diagnostic and Statistical Manual, Fifth Edition (DSM-5, DSM-V), the contents of which are incorporated by reference herein, including but not limited to: at least one of intrusive thoughts, nightmares, flashbacks, emotional distress after exposure to traumatic reminders, and physical reactivity after exposure to traumatic reminders; at least one of trauma-related thoughts or feelings and trauma-related reminders; at least two of inability to recall key features of the trauma, overly negative thoughts and assumptions about oneself or the world, exaggerated blame of self or others for causing the trauma, negative affect, decreased interest in activities, feeling isolated, and difficulty experiencing positive affect; and at least two of irritability or aggression, risky or destructive behavior, hypervigilance, heightened startle reaction, difficulty concentrating, and difficulty sleeping. Assessment of PTSD symptoms, or any of the symptoms of the present disclosure, can be performed using methods known in the art.

As used above and throughout the disclosure the term "effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with respect to the particular compound, component or composition selected, the route of administration, and the ability of the components to elicit a desired result in the individual, but also with respect to factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage being at the discretion of the attending physician. Dosage regimes may be adjusted to provide improved therapeutic response. An effective amount is also one in which any toxic or detrimental effects of the components are outweighed by the therapeutically beneficial effects.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

Within the present invention, the disclosed compounds may be prepared in the form of pharmaceutically acceptable salts. "Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein can be prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxy groups often exist in equilibrium with their zwitterionic forms. Thus, any of the compounds described herein that contain, for example, both amino and carboxy groups, also include reference to their corresponding zwitterions.

The term "stereoisomers" refers to compounds that have identical chemical constitution, but differ as regards the arrangement of the atoms or groups in space. The term "enantiomers" refers to stereoisomers that are mirror images of each other that are non-superimposable.

The term "administering" means either directly administering a compound or composition of the present invention, or administering a prodrug, derivative or analog which will form an equivalent amount of the active compound or substance within the body.

The terms "subject," "individual," and "patient" are used interchangeably herein, and refer to an animal, for example a human, to whom treatment, including prophylactic treatment, with the pharmaceutical composition according to the present invention, is provided. The term "subject" as used herein refers to human and non-human animals. The terms "non-human animals" and "non-human mammals" are used interchangeably herein and include all vertebrates, e.g., mammals, such as non-human primates, (particularly higher primates), sheep, dog, rodent, (e.g. mouse or rat), guinea pig, goat, pig, cat, rabbits, cows, horses and non-mammals such as reptiles, amphibians, chickens, and turkeys.

The term "inhibitor" as used herein includes compounds that inhibit the expression or activity of a protein, polypeptide or enzyme and does not necessarily mean complete inhibition of expression and/or activity. Rather, the inhibition includes inhibition of the expression and/or activity of a protein, polypeptide or enzyme to an extent, and for a time, sufficient to produce the desired effect.

While not intending to be bound by any particular mechanism of operation, it is believed that the methods of the present invention treat PTSD and other stress-related disorders by decreasing the amount of catecholamines secreted into the bloodstream.

Methods of treating intestinal PTSD and other stress-related disorders in a subject are provided. Such methods can include administering to a subject in need thereof an effective amount of a tyrosine hydroxylase inhibitor. Other such methods include administering to a subject in need thereof an effective amount of tyrosine hydroxylase inhibitor and an effective amount of one or more stress modulators.

This tyrosine hydroxylase inhibitor and the stress modulator can be administered simultaneously or sequentially. In some aspects, the stress modulator is administered at bedtime.

Administration of the tyrosine hydroxylase inhibitor or the tyrosine hydroxylase inhibitor and the stress modulator can be through various routes, including orally, nasally subcutaneously, intravenously, intramuscularly, transdermally, vaginally, rectally or in any combination thereof. Transdermal administration can be effected using, for example, oleic acid, 1-methyl-2-pyrrolidone, dodecylnonaoxyethylene glycol monoether.

In other suitable embodiments of the invention the tyrosine hydroxylase inhibitor and the stress modulator are administered daily or during a cycle consisting of five to seven days of administering the tyrosine hydroxylase inhibitor and the stress modulator, and one to two days of not administering the tyrosine hydroxylase inhibitor and the stress modulator. In some suitable embodiments of the invention, at least six of said cycles of administration are performed. In some suitable embodiments of the invention, 25-500 mg of the tyrosine hydroxylase inhibitor is administered either as a single dose or in divided doses.

In certain embodiments, the tyrosine hydroxylase inhibitor is a tyrosine derivative. The tyrosine derivative can be capable of existing in different isomeric forms, including stereoisomers and enantiomers. The tyrosine derivative can, for example, exist in L-form or D-form. The tyrosine derivative can, for example, also exist in a racemic form. Representative tyrosine derivatives include one or more of methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate H-D-Tyr (TBU)-allyl ester HCl, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy] phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy] benzyl malonate, methyl (2R)-2-amino-3-(3-chloro-4-methoxyphenyl)propanoate, methyl (2R)-2-amino-3-(3-chloro-4-hydroxy-5-methoxyphenyl) propanoate,methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyr-OMe HCl, H-3,5-diiodo-tyr-OMe HCl, H-D-3,5-diiodo-tyr-OMe HCl, H-D-tyr-OMe HCl, D-tyrosine methyl ester hydrochloride, D-tyrosine-OMe HCl, methyl D-tyrosinate hydrochloride, (2R)-2-amino-3-(4-hydroxyphenyl) propionic acid, (2R)-2-amino-3-(4-hydroxyphenyl) methyl ester hydrochloride, methyl (2R)-2-amino-3-(4-hydroxyphenyl) propanoate hydrochloride, methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-Tyr(3,5-I$_2$)—OSu, Fmoc-tyr(3-NO$_2$)—OH, and α-methyl-DL-tyrosine. In certain embodiments of the invention, the tyrosine derivative is α-methyl-L-tyrosine. In other embodiments, the tyrosine derivative is α-methyl-D-tyrosine. In other embodiments, the tyrosine derivative is α-methyl-DL-tyrosine in a racemic form.

In certain methods of the invention, 60 mg of the tyrosine derivative is administered orally and 0.25 mL of a 2 mg/mL suspension of the tyrosine derivative is administered subcutaneously. Preferably, 50-1500 mg of α-methyl-DL-tyrosine is administered daily.

Representative stress modulators include vasopressin, vasopressin derivatives, acetylcholine inducers, GABA, and other agents known to be useful in the treatment of anxiety or agitation, including but not limited to drugs in the benzodiazepine class or selective serotonin reuptake inhibitors (SSRIs). Vasopressin derivatives include 1-deamino-8-D-arginine vasopressin (DDAVP), 1-deamino-4-valin-8-D-arginine vasopressin (DVDAVP) and 8-arginine vasopressin (AVP). Acetylcholine inducers include both direct and indirect acetylcholine agonists such as melanotans, vasopressin, desmopressin, bethanechol, carbachol, cevimeline, pilocarpine, ambenomium, demecarium, donezepil, edrophonium, galantamine, neostigmine, physostigmine, pyridostigmine, rivastigmine, tacrine, and echotiophate (including salts thereof. Representative benzodiazepine drugs include clorazepate, diazepam, flurazepam, halazepam, prazepam, lorazepam, lormetazepam, oxazepam, temazepam, clonazepam, flunitrazepam, nimetazepam, nitrazepam, adinazolam, alprazolam, estazolam, triazolam, climazolam, loprazolam, and midazolam. Representative SSRIs include citalopram, fluvoxamine, escitalopram, paroxetine, sertraline, and fluoxetine (including salts thereof).

Representative subjects include mammals. In certain embodiments, the mammal is a human.

In some embodiments of the invention, methods further comprise assessing in the subject one or more symptoms of the stress-related disorder and/or the level of one or more metabolic agents, including bile acids, insulin, glucagon-like peptide, triglycerides, or fatty acids. This assessing step can be performed before said administering step or after said administering step.

The levels of catecholamines in a subject can be determined using any method known in the art, although methods that determine their levels in plasma and/or urine typically are employed.

Administration of pharmaceutically active molecules can be through various routes, including orally, nasally, subcutaneously, intravenously, intramuscularly, transdermally, vaginally, rectally or in any combination thereof. Transdermal administration can be effected using, for example, oleic acid, 1-methyl-2-pyrrolidone, dodecylnonaoxyethylene glycol monoether.

Also provided herein are kits comprising a tyrosine hydroxylase inhibitor and a stress modulator together with packaging for same. The tyrosine hydroxylase inhibitor can be a tyrosine derivative. The tyrosine derivative can include tyrosine derivatives capable of existing in isomeric form. The tyrosine derivatives can include tyrosine derivatives in its L-form or in its D-form. The tyrosine derivative can, for example, also exist in a racemic form. Representative tyrosine derivatives include one or more of methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate H-D-Tyr(TBU)-allyl ester HCl, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy] phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy] benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyr-OMe HCl, H-3,5-diiodo-tyr-OMe HCl, H-D-3,5-diiodo-tyr-OMe HCl, H-D-tyr-OMe HCl, D-tyrosine methyl ester hydrochloride, D-tyrosine-OMe HCl, methyl D-tyrosinate hydrochloride, (2R)-2-amino-3-(4-hydroxyphenyl) propionic acid, (2R)-2-amino-3-(4-hydroxyphenyl) methyl ester hydrochloride, methyl (2R)-2-amino-3-(4-hydroxyphenyl) propanoate hydrochloride, methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-Tyr(3,5-I$_2$)—OSu, Fmoc-tyr(3-NO$_2$)—OH, and α-methyl-DL-tyrosine. In certain embodiments of the invention, the tyrosine derivative is α-methyl-L-tyrosine. In other specific embodiments of the invention, the tyrosine derivative is α-methyl-D-tyrosine. In other embodiments, the tyrosine derivative is α-methyl-DL-tyrosine in a racemic form.

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

EXAMPLE 1

Patients are screened and the extent to which they meet the DSM-V criteria for PTSD is assessed. A subgroup of those satisfying the criteria are administered a treatment regimen that includes a tyrosine hydroxylase inhibitor (i.e., α-methyl-DL tyrosine) at dose of 200 mg three times daily. Another subgroup is administered a treatment regimen that further includes an acetylcholine inducer (e. g., a melanotan). GABA is optionally administered to both subgroups. Following each administration of the treatment regimen, changes in the extent to which the subjects satisfy the DSM-5 criteria are again assessed.

What is claimed:

1. A method of treating alleviating a symptom of post-traumatic stress disorder comprising orally administering to a subject in need thereof an effective amount of at least one tyrosine hydroxylase inhibitor; wherein said tyrosine hydroxylase inhibitor is one or more of methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate HD-Tyr(TBU)-allyl ester HCl, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy] phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy] benzyl malonate, methyl (2R)-2-amino-3-(3-chloro-4-methoxyphenyl)propanoate, methyl (2R)-2-amino-3-(3-chloro-4-hydroxy-5-methoxyphenyl) propanoate,methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyr-OMe HCl, H-3,5-diiodo-tyr-OMe HCl, H-D-3,5-diiodo-tyr-OMe HCl, H-D-tyr-OMe HCl, D-tyrosine methyl ester hydrochloride, D-tyrosine-OMe HCl, methyl D-tyrosinate hydrochloride, (2R)-2-amino-3-(4-hydroxyphenyl) propionic acid, (2R)-2-amino-3-(4-hydroxyphenyl) methyl ester hydrochloride, methyl (2R)-2-amino-3-(4-hydroxyphenyl) propanoate hydrochloride, methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-Tyr(3,5I2)-OSu, Fmoc-tyr(3-NO2)-OH, and α-methyl-DL-tyrosine.

2. The method of claim 1 wherein said at least one tyrosine hydroxylase inhibitor is α-methyl-DL-tyrosine.

3. The method of claim 1 further comprising administering to said subject an effective amount of one or more stress modulators.

4. The method of claim 3, wherein at least one stress modulator is vasopressin, a vasopressin derivative, an acetylcholine inducer, GABA, a benzodiazepine, or a selective serotonin reuptake inhibitor.

5. The method of claim 3 wherein the α-methyl-DL-tyrosine and the one or more stress modulators are administered simultaneously.

6. The method of claim 3, wherein the α-methyl-DL-tyrosine and the one or more stress modulators are administered separately.

7. The method of claim 2 wherein 50-1500 mg of the α-methyl-DL-tyrosine is administered daily.

8. The method of claim 2 wherein the α-methyl-DL-tyrosine is administered in three divided doses.

9. The method of claim 3 wherein the effective amount of the one or more stress modulators is administered daily.

10. The method of claim 1 wherein the symptom is at least one of the following: intrusive thoughts, nightmares, flashbacks, emotional distress after exposure to traumatic reminders, physical reactivity after exposure to traumatic reminders, trauma-related thoughts or feelings, trauma-related reminders, inability to recall key features of the trauma, overly negative thoughts and assumptions about oneself or the world, exaggerated blame of self or others for causing the trauma, negative affect, decreased interest in activities, feeling isolated, difficulty experiencing positive affect, irritability or aggression, risky or destructive behavior, hypervigilance, heightened startle reaction, difficulty concentrating, and difficulty sleeping.

* * * * *